(12) United States Patent
Xing et al.

(10) Patent No.: US 10,792,646 B2
(45) Date of Patent: Oct. 6, 2020

(54) DEHYDROGENATION CATALYSTS

(71) Applicant: Clariant Corporation, Louisville, KY (US)

(72) Inventors: Rong Xing, Louisville, KY (US); Vladimir Fridman, Louisville, KY (US)

(73) Assignee: Clariant Corporation, Louisville, KY (US)

( * ) Notice: Subject to any disclaimer, the term of this patent is extended or adjusted under 35 U.S.C. 154(b) by 0 days.

(21) Appl. No.: 16/151,416

(22) Filed: Oct. 4, 2018

(65) Prior Publication Data
US 2019/0126242 A1    May 2, 2019

Related U.S. Application Data

(60) Provisional application No. 62/578,677, filed on Oct. 30, 2017.

(51) Int. Cl.
*B01J 21/06* (2006.01)
*B01J 21/08* (2006.01)
(Continued)

(52) U.S. Cl.
CPC .............. *B01J 23/62* (2013.01); *B01J 21/04* (2013.01); *B01J 21/08* (2013.01); *B01J 23/002* (2013.01); *B01J 23/08* (2013.01); *B01J 23/63* (2013.01); *B01J 37/0201* (2013.01); *B01J 37/08* (2013.01); *C07C 5/00* (2013.01); *C07C 5/322* (2013.01); *C07C 5/3332* (2013.01); *C07C 5/3337* (2013.01); *B01J 2523/13* (2013.01); *B01J 2523/32* (2013.01); *B01J 2523/47* (2013.01); *B01J 2523/48* (2013.01);
(Continued)

(58) Field of Classification Search
CPC ... B01J 21/06; B01J 23/62; B01J 23/63; B01J 2523/13; B01J 2523/32; B01J 2523/47; B01J 2523/48; C07C 5/332; C07C 5/3337; C07C 2521/06; C07C 2523/62
See application file for complete search history.

(56) References Cited

U.S. PATENT DOCUMENTS

| 3,198,749 A | 8/1965 | Gladrow |
| 4,056,576 A | 11/1977 | Gregory |

(Continued)

FOREIGN PATENT DOCUMENTS

EP    1074299    2/2001

OTHER PUBLICATIONS

Machine translation of EP1074299, publication date Feb. 7, 2001.*

*Primary Examiner* — Jun Li

(57) ABSTRACT

This disclosure relates to catalyst compositions including gallium and a zirconium-based mixed oxide support, to methods for making such catalysts, and to methods for dehydrogenating hydrocarbons with such catalysts. For example, in one embodiment, a catalyst composition includes a mixed oxide support comprising at least about 50 wt. % of zirconium oxide, the mixed oxide support being present in the composition in an amount within the range of about 40 wt. % to about 99.9 wt. %; and disposed on the support, gallium, present in the composition in an amount within the range of about 0.1 wt. % to about 30 wt. %, calculated as $Ga_2O_3$ on a calcined basis.

14 Claims, 3 Drawing Sheets

(51) Int. Cl.
*B01J 23/08* (2006.01)
*B01J 37/02* (2006.01)
*B01J 37/08* (2006.01)
*B01J 23/62* (2006.01)
*B01J 23/00* (2006.01)
*C07C 5/32* (2006.01)
*B01J 21/04* (2006.01)
*B01J 23/63* (2006.01)
*C07C 5/00* (2006.01)
*C07C 5/333* (2006.01)
*C07C 11/09* (2006.01)

(52) U.S. Cl.
CPC ......... *B01J 2523/828* (2013.01); *C07C 11/09* (2013.01); *C07C 2521/06* (2013.01); *C07C 2523/08* (2013.01); *C07C 2523/62* (2013.01)

(56) References Cited

U.S. PATENT DOCUMENTS

| | | |
|---|---|---|
| 5,258,567 A | 11/1993 | Kerby |
| 5,346,871 A | 9/1994 | Robbins |
| 5,414,182 A | 5/1995 | Iezzi |
| 6,031,143 A | 2/2000 | Buonomo |
| 7,235,706 B2 | 6/2007 | Iezzi |
| 8,151,573 B2 | 4/2012 | Christopher |
| 8,653,317 B2 | 2/2014 | Luo |
| 9,776,170 B2 | 11/2017 | Kaminsky |
| 2010/0274011 A1* | 10/2010 | Kubanek ............... B01J 23/002 544/178 |
| 2014/0274672 A1* | 9/2014 | Kauffman ............ B01J 27/1853 502/213 |
| 2016/0288093 A1* | 10/2016 | Kaminsky ............. C07C 5/3332 |

* cited by examiner

DEHYDROGENATION CATALYSTS

CROSS-REFERENCE TO RELATED APPLICATIONS

This application claims the benefit of priority of U.S. Provisional Patent Application No. 62/578,677, filed Oct. 30, 2017, which is hereby incorporated herein by reference in its entirety.

BACKGROUND OF THE DISCLOSURE

Field of the Disclosure

This disclosure relates generally to catalyst materials. More particularly, the present disclosure relates to catalysts comprising gallium and a mixed oxide support useful in the dehydrogenation of hydrocarbons, to methods for making such catalysts, and to methods for dehydrogenating hydrocarbons with such catalysts.

Technical Background

Alkane dehydrogenation is a recognized process for production of a variety of useful hydrocarbon products, such as in the dehydrogenation of propane to make propene for use in the polymer industry, dehydrogenation of n-butane to produce n-butene or alkylate and butadiene useful in tire production, and the dehydrogenation of isobutane to make isobutylene suitable for conversion to methyl tert-butyl ether, isooctane, and alkylates to supplement and enrich gasolines. Current commercial catalysts useful for catalytic dehydrogenation of light alkanes include $CrOx/Al_2O_3$ and $Pt-Sn/Al_2O_3$ catalysts, which have been in use for decades.

$CrOx/Al_2O_3$ dehydrogenation catalysts typically contain a majority of their chromium in the Cr(III) oxidation state. However, there typically remains a small amount of Cr(VI), which is carcinogenic and thus presents health risks during catalyst handling and operation. $Pt-Sn/Al_2O_3$ catalysts are expensive. Moreover, to provide a spent $Pt-Sn/Al_2O_3$ catalyst with initial activity, the treatment during operation with $Cl_2$-containing gas is required. Such gases can be deadly and thus present significant risks during operation. They also can cause significant environmental chlorine pollution.

Gallium-based dehydrogenation catalysts have been known for about two decades. They are generally not hazardous, and their application presents no significant environmental issues. However, these catalysts have limitations in activity and stability, especially for the commercially important dehydrogenation of propane, n-butane and isobutane.

Accordingly, there remains a need for gallium-based dehydrogenation catalysts that provide improved activity and stability, especially in the dehydrogenation of isobutane.

SUMMARY OF THE DISCLOSURE

One aspect of the disclosure is a calcined dehydrogenation catalyst composition comprising a mixed oxide support comprising at least about 50 wt. % of zirconium oxide, the mixed oxide support being present in the composition in an amount within the range of about 40 wt. % to about 99.9 wt. %; and gallium disposed on the support and present in the composition in an amount within the range of about 0.1 wt. % to about 30 wt. %, calculated as $Ga_2O_3$ on a calcined basis.

Another aspect of the disclosure is a method for preparing a dehydrogenation catalyst composition as described herein, the method comprising providing a mixed oxide support comprising at least about 50 wt. % of zirconium oxide; disposing on the mixed oxide support one or more sources of gallium and of any primary or secondary promoters and cerium to be present in the catalyst composition; and calcining the supported composition so formed.

a mixed oxide support comprising at least about 50 wt. % of zirconium oxide, the mixed oxide support being present in the composition in an amount within the range of about 40 wt. % to about 99.9 wt. %; and Another aspect of the disclosure is a dehydrogenation catalyst prepared by a method described herein.

Another aspect of the disclosure is a method for dehydrogenating hydrocarbons, the method comprising contacting a hydrocarbon feed with the catalyst composition as described herein.

Other aspects of the disclosure will be apparent to the person of ordinary skill in the art in view of the disclosure herein.

DETAILED DESCRIPTION

Figure 1:
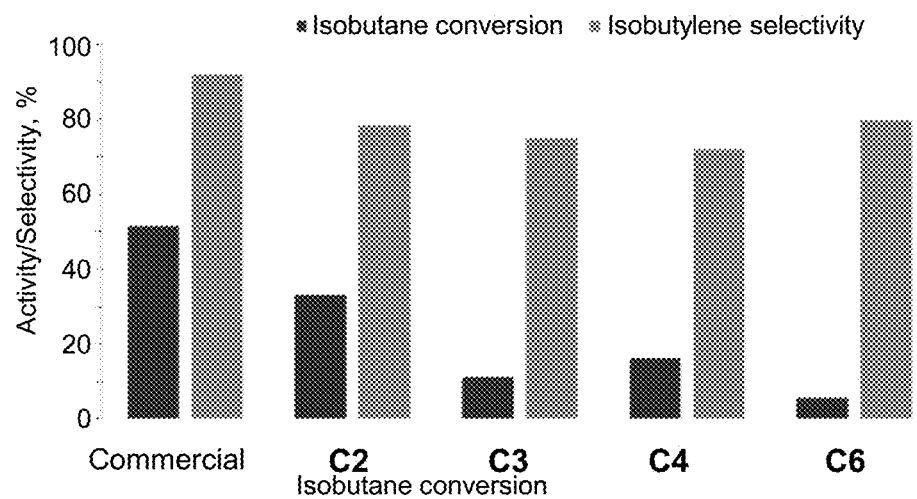
FIG. 1 is a bar graph showing (left-to-right in each set of bars) isobutane dehydrogenation conversion and isobutylene selectivity data for a variety of catalysts described herein.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparatuses, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The disclosure relates to calcined dehydrogenation catalyst compositions that include a mixed oxide support and gallium (e.g., in the form of an oxide thereof). The disclosure demonstrates that such catalysts, which may be free of chromium-containing materials, exhibit activity comparable to or higher than $CrO_x/Al_2O_3$ catalysts and/or silica- and alumina-supported catalysts.

One aspect of the disclosure is a calcined dehydrogenation catalyst composition. The catalyst composition includes a mixed oxide support including at least about 50 wt. % of zirconium oxide, the mixed oxide support being present in the composition in an amount within the range of about 40 wt. % to about 99.9 wt. %; and disposed on the support, gallium, present in the composition in an amount within the range of about 0.1 wt. % to about 30 wt. %, calculated as $Ga_2O_3$ on a calcined basis. In certain embodiments as described herein, a catalyst composition includes, disposed on the support, one or more primary promoters selected from platinum, iridium, lanthanum, zinc, iron, rhodium, palladium, and ruthenium, present in the composition in an amount within the range of about 0.01 wt. % to about 5 wt. %, calculated as an oxide on a calcined basis. And in certain embodiments as described herein, a catalyst composition includes, disposed on the support, one or more secondary promoters selected from potassium, sodium, cesium, lithium, calcium, magnesium, strontium, and barium, present in the composition in an amount within the range of about 0.01 wt. % to about 15 wt. %. The mixed oxide support can, in certain embodiments of the catalyst compositions as otherwise described herein, include an oxide of one or more of lanthanum, cerium, silicon, titanium, tungsten, and yttrium.

As used herein, the term "oxide," including, e.g., "mixed oxide," "gallium oxide," etc., includes oxides in all forms and crystalline phase. For example, "gallium oxide" includes $Ga_2O_3$, $Ga_2O_x$ wherein x is within the range of 1 to 3, etc. Unless otherwise indicated, regardless of the actual stoichiometry of the oxide, oxides are calculated as the most stable oxide for purposes of weight percent determinations. For example, the person of ordinary skill in the art will appreciate that a non-stoichiometric oxide of gallium, or even another form of gallium, may still be calculated as $Ga_2O_3$. Moreover, unless otherwise indicated, the compositions are described on an as-calcined basis.

Without intending to be bound by theory, the present inventors believe that the gallium acts as the primary catalytic species in dehydrogenation reactions mediated by the catalyst compositions described herein. As described above, in one aspect of the compositions of the disclosure, gallium is present in an amount within the range of about 0.1 wt. % to about 30 wt. %, calculated as $Ga_2O_3$. For example, in certain embodiments of the compositions as otherwise described herein, gallium is present in an amount within the range of about 0.1 wt. % to about 27.5 wt. %, or about 0.1 wt. % to about 25 wt. %, or about 0.1 wt. % to about 22.5 wt. %, or about 0.1 wt. % to about 20 wt. %, or about 0.1 wt. % to about 17.5 wt. %, or about 0.1 wt. % to about 15 wt. %, or about 0.1 wt. % to about 12.5 wt. %, or about 0.1 wt. % to about 10 wt. %, or about 0.5 wt. % to about 30 wt. %, or about 1 wt. % to about 30 wt. %, or about 2.5 wt. % to about 30 wt. %, or about 5 wt. % to about 30 wt. %, or about 7.5 wt. % to about 30 wt. %, or about 10 wt. % to about 30 wt. %, or about 12.5 wt. % to about 30 wt. %, or about 15 wt. % to about 30 wt. %, or about 17.5 wt. % to about 30 wt. %, or about 20 wt. % to about 30 wt. %, or about 0.5 wt. % to about 27.5 wt. %, or about 0.5 wt. % to about 25 wt. %, or about 1 wt. % to about 22.5 wt. %, or about 1 wt. % to about 20 wt. %, or about 2 wt. % to about 17.5 wt. %, or about 3 wt. % to about 15 wt. %, calculated as $Ga_2O_3$ on a calcined basis.

In certain embodiments of the compositions as otherwise described herein, the catalyst composition further comprises one or more primary promoters selected from platinum, iridium, lanthanum, zinc, iron, rhodium, palladium, and ruthenium. For example, in certain embodiments of the compositions as otherwise described herein, one or more primary promoters selected from platinum, iridium, lanthanum, zinc, iron, rhodium, palladium, and ruthenium are present in a total amount within the range of about 0.01 wt. % to about 5 wt. %. In certain embodiments of the compositions as otherwise described herein, one or more primary promoters selected from platinum, iridium, lanthanum, zinc, iron, rhodium, palladium, and ruthenium are present in a total amount within the range of about 0.01 wt. % to about 4.5 wt. %, or about 0.01 wt. % to about 4 wt. %, or about 0.01 wt. % to about 3.5 wt. %, or about 0.01 wt. % to about 3 wt. %, or about 0.01 wt. % to about 2.5 wt. %, or about 0.01 wt. % to about 2 wt. %, or about 0.01 wt. % to about 1.5 wt. %, or about 0.01 wt. % to about 1 wt. %, or about 0.01 wt. % to about 0.5 wt. %, or about 0.025 wt. % to about 5 wt. %, or about 0.05 wt. % to about 5 wt. %, or about 0.075 wt. % to about 5 wt. %, or about 0.1 wt. % to about 5 wt. %, or about 0.25 wt. % to about 5 wt. %, or about 0.5 wt. % to about 5 wt. %, or about 0.75 wt. % to about 5 wt. %, or about 1 wt. % to about 5 wt. %, or about 1.5 wt. % to about 5 wt. %, or about 2 wt. % to about 5 wt. %, or about 2.5 wt. % to about 5 wt. %, or about 3 wt. % to about 5 wt. %, or about 0.05 wt. % to about 4.5 wt. %, or about 0.075 wt. % to about 4 wt. %, or about 0.1 wt. % to about 3.5 wt. %, or about 0.25 wt. % to about 3 wt. %, or about 0.5 wt. % to about 2.5 wt. %, calculated as oxide on a calcined basis.

For example, in certain embodiments of the compositions as otherwise described herein, platinum is disposed on the support, for example, in an amount within the range of about 0.005 wt. % to about 5 wt. %, for example, about 0.005 wt. % to about 1 wt. % of the composition, calculated as $PtO_2$ on a calcined basis.

In certain embodiments of the compositions as otherwise described herein, ruthenium is disposed on the support, for example, in an amount within the range of about 0.01 wt. % to about 5 wt. %, for example, about 0.01 wt. % to about 1 wt. % of the composition, calculated as $RuO_2$ on a calcined basis.

In certain embodiments of the compositions as otherwise described herein, iridium is disposed on the support, for example, in an amount within the range of about 0.01 wt. % to about 5 wt. %, for example, about 0.01 wt. % to about 1 wt. % of the composition, calculated as $IrO_2$ on a calcined basis.

In certain embodiments of the compositions as otherwise described herein, lanthanum is disposed on the support, for example, in an amount within the range of about 0.01 wt. % to about 5 wt. %, for example, about 0.01 wt. % to about 1 wt. % of the composition, calculated as $La_2O_3$ on a calcined basis.

In certain embodiments of the compositions as otherwise described herein, zinc is disposed on the support, for example, in an amount within the range of about 0.01 wt. % to about 5 wt. %, for example, about 0.01 wt. % to about 1 wt. % of the composition, calculated as $ZnO_2$ on a calcined basis.

In certain embodiments of the compositions as otherwise described herein, iron is disposed on the support, for example, in an amount within the range of about 0.01 wt. % to about 5 wt. %, for example, about 0.01 wt. % to about 1 wt. % of the composition, calculated as $Fe_2O_3$ on a calcined basis.

In certain embodiments of the compositions as otherwise described herein, manganese is disposed on the support, for example, in an amount within the range of about 0.01 wt. % to about 5 wt. %, for example, about 0.01 wt. % to about 1 wt. % of the composition, calculated as $MnO_2$ on a calcined basis.

In certain embodiments of the compositions as otherwise described herein, the catalyst composition further comprises (e.g., together with the one or more primary promoters) one or more secondary promoters selected from potassium, sodium, cesium, lithium, gallium, magnesium, strontium, and barium. For example, in certain embodiments of the compositions as otherwise described herein, one or more secondary promoters are present, in a total amount within the range of about 0.01 wt. % to about 15 wt. %. In certain embodiments of the compositions as otherwise described herein, one or more secondary promoters selected from potassium, sodium, cesium, lithium, gallium, magnesium, strontium, and barium are present in a total amount within the range of about 0.01 wt. % to about 12.5 wt. %, or about 0.01 wt. % to about 10 wt. %, or about 0.01 wt. % to about 7.5 wt. %, or about 0.01 wt. % to about 5 wt. %, or about 0.01 wt. % to about 4 wt. %, or about 0.01 wt. % to about 3 wt. %, or about 0.01 wt. % to about 2 wt. %, or about 0.025 wt. % to about 15 wt. %, or about 0.05 wt. % to about 15 wt. %, or about 0.075 wt. % to about 15 wt. %, or about 0.1 wt. % to about 15 wt. %, or about 0.25 wt. % to about 15 wt. %, or about 0.5 wt. % to about 15 wt. %, or about 0.75 wt. % to about 15 wt. %, or about 1 wt. % to about 15 wt. %, or about 1.5 wt. % to about 15 wt. %, or about 2 wt. % to about 15 wt. %, or about 2.5 wt. % to about 15 wt. %, or about 5 wt. % to about 15 wt. %, or about 7.5 wt. % to about 15 wt. %, or about 0.025 wt. % to about 12.5 wt. %, or about 0.05 wt. % to about 10 wt. %, calculated as oxide on a calcined basis.

In certain embodiments of the compositions as otherwise described herein, potassium is disposed on the support, for example, in an amount within the range of about 0.01 wt. % to about 15 wt. %, e.g., about 0.01 wt. % to about 2 wt. %, calculated as $K_2O$ on a calcined basis.

In certain embodiments of the compositions as otherwise described herein, magnesium is disposed on the support, for example, in an amount within the range of about 0.01 wt. % to about 15 wt. %, e.g., about 0.01 wt. % to about 2 wt. %, calculated as MgO on a calcined basis.

In certain embodiments of the compositions as otherwise described herein, sodium is disposed on the support, for example, in an amount within the range of about 0.01 wt. % to about 15 wt. %, e.g., about 0.01 wt. % to about 2 wt. %, calculated as $Na_2O$ on a calcined basis.

In certain embodiments of the compositions as otherwise described herein, cesium is disposed on the support, for example, in an amount within the range of about 0.01 wt. % to about 15 wt. %, e.g., about 0.01 wt. % to about 2 wt. %, calculated as $Cs_2O$ on a calcined basis.

In certain embodiments of the compositions as otherwise described herein, lithium is disposed on the support, for example, in an amount within the range of about 0.01 wt. % to about 15 wt. %, e.g., about 0.01 wt. % to about 2 wt. %, calculated as $Li_2O$ on a calcined basis.

In certain embodiments of the compositions as otherwise described herein, calcium is disposed on the support, for example, in an amount within the range of about 0.01 wt. % to about 15 wt. %, e.g., about 0.01 wt. % to about 2 wt. %, calculated as CaO on a calcined basis.

In certain embodiments of the compositions as otherwise described herein, strontium is disposed on the support, for example, in an amount within the range of about 0.01 wt. % to about 15 wt. %, e.g., about 0.01 wt. % to about 2 wt. %, calculated as SrO on a calcined basis.

In certain embodiments of the compositions as otherwise described herein, barium is disposed on the support, for example, in an amount within the range of about 0.01 wt. % to about 15 wt. %, e.g., about 0.01 wt. % to about 2 wt. %, calculated as BaO on a calcined basis.

In certain embodiments as otherwise described herein, the catalyst composition comprises, disposed on the support, cerium oxide. For example, in certain embodiments of the compositions as otherwise described herein, cerium oxide is present disposed on the support in an amount within the range of about 0.5 wt. % to about 15 wt. %, e.g., about 0.5 wt. % to about 12.5 wt. %, or about 0.5 wt. % to about 10 wt. %, or about 0.5 wt. % to about 7.5 wt. %, or about 0.5 wt. % to about 5 wt. %, or about 0.5 wt. % to about 4.5 wt. %, or about 0.5 wt. % to about 4 wt. %, or about 0.5 wt. % to about 3.5 wt. %, or about 0.5 wt. % to about 3 wt. %, or about 0.5 wt. % to about 2.5 wt. %, or about 0.75 wt. % to about 15 wt. %, or about 1 wt. % to about 15 wt. %, or about 1.5 wt. % to about 15 wt. %, or about 2 wt. % to about 15 wt. %, or about 2.5 wt. % to about 15 wt. %, or about 3 wt. % to about 15 wt. %, or about 4 wt. % to about 15 wt. %, or about 5 wt. % to about 15 wt. %, or about 6 wt. % to about 15 wt. %, or about 7 wt. % to about 15 wt. %, or about 8 wt. % to about 15 wt. %, or about 9 wt. % to about 15 wt. %, or about 10 wt. % to about 15 wt. %, or about 0.75 wt. % to about 12.5 wt. %, or about 1 wt. % to about 10 wt. %, or about 2 wt. % to about 9 wt. %, or about 3 wt. % to about 8 wt. %, calculated as $CeO_2$ on a calcined basis. Without intending to be bound by theory, the inventors believe that addition of cerium can further stabilize the material.

Notably, the catalyst compositions of the disclosure have a mixed oxide support comprising at least about 50 wt. % of zirconium oxide, present in the overall catalyst composition in an amount within the range of about 40 wt. % to about 99.9 wt. %. For example, in certain embodiments of the compositions as otherwise described herein, the mixed oxide support is present in the overall catalyst composition in an amount within the range of about 45 wt. % to about 99.9 wt. %, or about 50 wt. % to about 99.9 wt. %, or about 55 wt. % to about 99.9 wt. %, or about 60 wt. % to about 99.9 wt. %, or about 65 wt. % to about 99.9 wt. %, or about 70 wt. % to about 99.9 wt. %, or about 75 wt. % to about 99.9 wt. %, or about 80 wt. % to about 99.9 wt. %, or about 40 wt. % to about 99.5 wt. %, or about 40 wt. % to about 99 wt. %, or about 40 wt. % to about 98 wt. %, or about 40 wt. % to about 95 wt. %, or about 40 wt. % to about 90 wt. %, or about 40 wt. % to about 85 wt. %, or about 40 wt. % to about 80 wt. %, or about 40 wt. % to about 75 wt. %, or about 40 wt. % to about 70 wt. %, or about 40 wt. % to about 65 wt. %, or about 40 wt. % to about 60 wt. %, or about 40 wt. % to about 55 wt. %, or about 45 wt. % to about 60 wt. %, or about 50 wt. % to about 65 wt. %, or about 55 wt. % to about 70 wt. %, or about 60 wt. % to about 75 wt. %, or about 65 wt. % to about 80 wt. %, or about 70 wt. % to about 85 wt. %, or about 70 wt. % to about 97 wt. %, or about 75 wt. % to about 90 wt. %, or about 80 wt. % to about 95 wt. %, or about 85 wt. % to about 99.9 wt. %.

The mixed oxide support includes one or more oxides other than zirconium. For example, in certain embodiments of the compositions as otherwise described herein, the mixed oxide support comprises an oxide of one or more of lanthanum, cerium, silicon, titanium, tungsten, and yttrium. In certain such embodiments, the total amount of oxides of zirconium, lanthanum, cerium, silicon, titanium, tungsten, and yttrium in the mixed oxide support is at least 80 wt. %, at least 90 wt. %, at least 95 wt. %, at least 98 wt. %, or even at least 99 wt. %. In certain embodiments as otherwise described herein, the mixed oxide support comprises an oxide of one or more of lanthanum, cerium, titanium, tungsten, and yttrium. In certain such embodiments, the total amount of oxides of zirconium, lanthanum, cerium, titanium, tungsten, and yttrium in the mixed oxide support is at least 80 wt. %, at least 90 wt. %, at least 95 wt. %, at least 98 wt. %, or even at least 99 wt. %.

In certain embodiments of the disclosure as otherwise described herein, the mixed oxide support comprises an oxide of one or more of lanthanum, silicon and cerium. For example, in certain embodiments of the compositions as otherwise described herein, the mixed oxide support comprises about 80 wt. % to about 99 wt. %, e.g., about 80 wt. % to about 85 wt. %, or about 85 wt. % to about 90 wt. %, or about 90 wt. % to about 95 wt. %, or about 95 wt. % to about 99 wt. % of zirconium oxide, and about 1 wt. % to about 20 wt. %, e.g., about 1 wt. % to about 5 wt. %, or about 5 wt. % to about 10 wt. %, or about 10 wt. % to about 15 wt. %, or about 15 wt. % to about 20 wt. % of an oxide of one or more of lanthanum, silicon and cerium. In certain such embodiments, the total amount of oxides of zirconium, lanthanum, silicon and cerium in the mixed oxide support is at least 80 wt. %, at least 90 wt. %, at least 95 wt. %, at least 98 wt. %, or even at least 99 wt. %.

In another example, in certain embodiments of the compositions as otherwise described herein, the mixed oxide support includes titanium oxide. For example, in certain such embodiments, the mixed oxide support comprises about 50 wt. % to about 75 wt. %, e.g., about 50 wt. % to about 55 wt. %, or about 55 wt. % to about 60 wt. %, or about 60 wt. % to about 65 wt. %, or about 65 wt. % to about 70 wt. %, or about 70 wt. % to about 75 wt. % of zirconium oxide, and about 25 wt. % to about 50 wt. %, e.g., about 25 wt. % to about 30 wt. %, or about 30 wt. % to about 35 wt. %, or about 35 wt. % to about 40 wt. %, or about 40 wt. % to about 45 wt. %, or about 45 wt. % to about 50 wt. % of titanium oxide. In certain such embodiments, the total amount of oxides of zirconium and titanium in the mixed oxide support is at least 80 wt. %, at least 90 wt. %, at least 95 wt. %, at least 98 wt. %, or even at least 99 wt. %.

In certain embodiments of the disclosure as otherwise described herein, the mixed oxide support comprises an oxide of one or more of yttrium and tungsten. For example, in certain embodiments of the compositions as otherwise described herein, the mixed oxide support comprises about 80 wt. % to about 99 wt. %, e.g., about 80 wt. % to about 85 wt. %, or about 85 wt. % to about 90 wt. %, or about 90 wt. % to about 95 wt. %, or about 95 wt. % to about 99 wt. % of zirconium oxide, and about 1 wt. % to about 20 wt. %, e.g., about 1 wt. % to about 5 wt. %, or about 5 wt. % to about 10 wt. %, or about 10 wt. % to about 15 wt. %, or about 15 wt. % to about 20 wt. % of an oxide of one or more of lanthanum, silicon and cerium. In certain such embodiments, the total amount of oxides of zirconium, yttrium and tungsten in the mixed oxide support is at least 80 wt. %, at least 90 wt. %, at least 95 wt. %, at least 98 wt. %, or even at least 99 wt. %.

The person of ordinary skill in the art will appreciate that the mixed oxide support may, in some embodiments as otherwise described herein, have low amounts of, or even be substantially free of alumina. For example, in certain embodiments of the compositions as otherwise described herein, the mixed oxide support includes less than about 5 wt. %, or less than about 4 wt. %, or less than about 3 wt. %, or less than about 2 wt. %, or less than about 1 wt. %, or less than about 0.05 wt. %, or less than about 0.01 wt. % of alumina.

The person of ordinary skill in the art will appreciate that the mixed oxide support may, in some embodiments as otherwise described herein, have low amounts of, or even be substantially free of silica. For example, in certain embodiments of the compositions as otherwise described herein, the mixed oxide support includes less than about 5 wt. %, or less than about 4 wt. %, or less than about 3 wt. %, or less than about 2 wt. %, or less than about 1 wt. %, or less than about 0.05 wt. %, or less than about 0.01 wt. % of silica.

In certain embodiments of the compositions as otherwise described herein, the composition comprises a mixed oxide support, present in an amount within the range of about 75 wt. % to about 99 wt. %, or about 83.5 wt. % to about 98.85 wt. %, and gallium, present in an amount within the range of about 1 wt. % to about 20 wt. %, or about 1 wt. % to about 15 wt. %. In certain such embodiments, the catalyst composition further comprises a platinum promoter, present in an amount within the range of about 0.05 wt. % to about 1 wt. %, or about 0.05 wt. % to about 0.5 wt. %. In certain such embodiments, the catalyst composition further comprises a potassium secondary promoter, present in an amount within the range of about 0.01 wt. % to about 2 wt. %, or about 0.1 wt. % to about 1 wt. %. In certain such embodiments, the mixed oxide support comprises about 80 wt. % to about 99 wt. % of zirconium oxide, and amount 1 wt. % to about 20 wt. % of an oxide of one or more of lanthanum, silicon, and cerium. In other such embodiments, the mixed oxide support comprises about 50 wt. % to about 75 wt. % of zirconium oxide, and about 25 wt. % to about 50 wt. % of titanium oxide.

The person of ordinary skill in the art will appreciate that the catalyst composition may be substantially free of chromium. For example, in certain embodiments of the compositions as otherwise described herein, the catalyst composition includes less than about 1 wt. %, or less than about 0.9 wt. %, or less than about 0.8 wt. %, or less than about 0.7 wt. %, or less than about 0.6 wt. %, or less than about 0.5 wt. %, or less than about 0.4 wt. %, or less than about 0.3 wt. %, or less than about 0.2 wt. %, or less than about 0.1 wt. %, or less than about 0.05 wt. %, or less than about 0.01 wt. % of chromium, calculated as $Cr_2O_3$.

The person of ordinary skill in the art will appreciate that the catalyst composition may be substantially free of each of lanthanides other than lanthanum and cerium. For example, in certain embodiments of the compositions as otherwise described herein, the catalyst composition includes less than about 1 wt. %, or less than about 0.9 wt. %, or less than about 0.8 wt. %, or less than about 0.7 wt. %, or less than about 0.6 wt. %, or less than about 0.5 wt. %, or less than about 0.4 wt. %, or less than about 0.3 wt. %, or less than about 0.2 wt. %, or less than about 0.1 wt. %, or less than about 0.05 wt. %, or less than about 0.01 wt. % of the lanthanides other than lanthanum and cerium, calculated as $La_2O_3$ and $CeO_2$, respectively.

In certain desirable embodiments of the compositions as otherwise described herein, the total amount of the mixed oxide support, gallium (e.g., in the form of gallium oxide of any crystalline phase), the one or more primary promoters (e.g., platinum, iridium, lanthanum, zinc, iron, rhodium, palladium, and ruthenium), the one or more secondary promoters (e.g., potassium, sodium, cesium, lithium, gallium, magnesium, strontium, and barium), and cerium oxide is at least about 80 wt. %, or at least about 85 wt. %, or at least about 90 wt. %, or at least about 95 wt. %, or at least about 97.5 wt. %, or at least about 99 wt. % of the composition.

Another aspect of the disclosure is a method for preparing a dehydrogenation catalyst composition as described herein. The method includes providing a mixed oxide support comprising at least about 50 wt. % of zirconium oxide, disposing one or more sources of gallium and of any primary or secondary promoters and cerium on the mixed oxide support (e.g., by impregnation), then calcining the supported composition. The amounts and identities of the various components (e.g., mixed oxide support, promoters, secondary promoters, and cerium oxide) can be as otherwise described above with respect to the catalyst compositions of the disclosure. The person of ordinary skill in the art can provide a gallium source suitable to provide the desired amounts of gallium. The person of ordinary skill in the art will use conventional methodologies to make the catalyst compositions of the disclosure, for example, using impregnation, co-precipitation, or sol-gel synthesis, based on the disclosure herein. The types of sources used will be provided by the person of ordinary skill in the art depending on the particular synthesis technique to be used; for example, salts such as nitrates can be used as metal sources when impregnation techniques are to be used.

As described above, the method includes calcining the supported composition (e.g., an impregnated support). In certain embodiments of the methods as otherwise described herein, the supported composition is calcined at a temperature within the range of about 250° C. to about 850° C. For example, in certain embodiments of the methods as otherwise described herein, the supported composition is calcined at a temperature within the range of about 250° C. to about 800° C., or about 250° C. to about 750° C., or about 250° C. to about 700° C., or about 250° C. to about 650° C., or about 250° C. to about 600° C., or about 250° C. to about 550° C., or about 250° C. to about 500° C., or about 300° C. to about 850° C., or about 350° C. to about 850° C., or about 350° C. to about 850° C., or about 400° C. to about 850° C., or about 450° C. to about 850° C., or about 500° C. to about 850° C., or about 300° C. to about 800° C., or about 350° C. to about 750° C., or about 400° C. to about 700° C., or about 450° C. to about 650° C., or about 500° C. to about 600° C.

In some embodiments of the methods as otherwise described herein, the supported composition is calcined for a period of time within the range of about 5 min. to about 12 hr. For example, in certain embodiments of the methods as otherwise described herein, the impregnated support is calcined for a period of time within the range of about 10 min. to about 12 hr., or about 15 min. to about 12 hr., or about 20 min. to about 12 hr., or about 30 min. to about 12 hr., or about 45 min. to about 12 hr., or about 1 hr. to about 12 hr., or about 1.5 hr. to about 12 hr., or about 2 hr. to about 12 hr., or about 5 min. to about 11 hr., or about 5 min. to about 10 hr., or about 5 min. to about 9 hr., or about 5 min. to about 8 hr., or about 5 min. to about 7.5 hr., or about 5 min. to about 7 hr., or about 5 min. to about 6.5 hr., or about 5 min. to about 6 hr., or about 5 min. to about 5.5 hr., or about 5 min. to about 5 hr., or about 30 min. to about 11 hr., or about 1 hr. to about 10 hr., or about 1.5 hr. to about 9 hr., or about 2 hr. to about 8 hr.

In some embodiments of the methods as otherwise described herein, the supported composition is dried before calcination (e.g., especially in the case of impregnation-based methods). In some embodiments of the methods as otherwise described herein, the supported composition is dried at a temperature within the range of about 40° C. to about 200° C. For example, in certain embodiments of the methods as otherwise described herein, the supported composition is dried at a temperature within the range of about 60° C. to about 200° C., or about 80° C. to about 200° C., or about 100° C. to about 200° C., or about 40° C. to about 180° C., or about 40° C. to about 160° C., or about 40° C. to about 140° C., or about 60° C. to about 180° C., or about 80° C. to about 160° C., or about 100° C. to about 140° C.

In some embodiments of the methods as otherwise described herein, the supported composition is dried for a period of time within the range of about 4 hr. to about 36 hr. For example, in certain embodiments of the methods as otherwise described herein, the supported composition is dried for a period of time within the range of about 4 hr. to about 30 hr., or about 4 hr. to about 24 hr., or about 4 hr. to about 22 hr., or about 4 hr. to about 20 hr., or about 6 hr. to about 36 hr., or about 8 hr. to about 36 hr., or about 10 hr. to about 36 hr., or about 12 hr. to about 36 hr., or about 6 hr. to about 30 hr., or about 8 hr. to about 24 hr., or about 10 hr. to about 22 hr., or about 12 hr. to about 20 hr.

Another aspect of the disclosure is a catalyst composition prepared by a method as described herein.

Advantageously, the present inventors have determined that use of catalyst compositions described herein can catalyze a hydrocarbon dehydrogenation reaction at an efficiency comparable to or better than conventional chromium-containing or alumina- and/or silica-supported catalyst materials.

The compositions described herein are especially useful in hydrocarbon dehydrogenation reactions. Accordingly, another aspect of the disclosure is a method for dehydrogenating alkanes that includes contacting a hydrocarbon feed with a catalyst composition as described herein under conditions sufficient to cause hydrocarbon dehydrogenation.

In some embodiments of the dehydrogenation methods as otherwise described herein, the hydrocarbon feed comprises one or more $C_3$-$C_5$ alkanes. For example, in certain embodiments of the dehydrogenation methods as otherwise described herein, the hydrocarbon feed comprises mainly of isobutane. For example, in certain embodiments of the dehydrogenation methods as otherwise described herein, the hydrocarbon feed comprises mainly of propane.

The contacting of the feed with the catalyst compositions described herein can be conducted in a variety of ways familiar to the person of ordinary skill in the art. Conventional equipment and processes can be used in conjunction with the catalyst compositions of the disclosure to provide beneficial performance. Thus, the catalyst may be contained in one bed within a reactor vessel or divided up among a plurality of beds within a reactor. The reaction system may contain one or more reaction vessels in series. The feed to the reaction zone can flow vertically upwards, or downwards through the catalyst bed in a typical plug flow reactor, or horizontally across the catalyst bed in a radial flow type reactor.

The contacting of the feed with the catalyst composition can be performed using conventional methods. For example, the feed may be introduced into the reaction zone containing the catalyst composition at a constant rate, or alternatively, at a variable rate.

In certain embodiments of the dehydrogenation methods as otherwise described herein, the feed is contacted with the provided catalyst composition at a liquid hourly space velocity (LHSV) within the range of about 0.1 $h^{-1}$ to about 2 $h^{-1}$. For example, in certain embodiments of the dehydrogenation methods as otherwise described herein, the feed is contacted with the provided catalyst composition at a liquid hourly space velocity of about 0.1 $h^{-1}$ to about 1.75 $h^{-1}$, or about 0.1 $h^{-1}$ to about 1.5 $h^{-1}$, or about 0.1 $h^{-1}$ to about 1.25 $h^{-1}$, or about 0.1 $h^{-1}$ to about 1.0 $h^{-1}$, or about 0.1 $h^{-1}$ to about 0.75 $h^{-1}$, or about 0.1 $h^{-1}$ to about 5 $h^{-1}$, or about 0.25 $h^{-1}$ to about 2 $h^{-1}$, or about 0.5 $h^{-1}$ to about 2 $h^{-1}$, or about 0.75 $h^{-1}$ to about 2 $h^{-1}$, or about 1 $h^{-1}$ to about 2 $h^{-1}$, or about 1.25 h$^{-1}$ to about 2 h$^{-1}$, or about 1.5 h$^{-1}$ to about 2 h$^{-1}$, or about 0.25 h$^{-1}$ to about 1.75 h$^{-1}$, or about 0.5 h$^{-1}$ to about 1.5 h$^{-1}$, or about 0.75 h$^{-1}$ to about 1.25 h$^{-1}$.

In certain embodiments of the dehydrogenation methods as otherwise described herein, the method is carried out at a temperature within the range of about 400° C. to about 750° C. For example, in certain embodiments of the dehydrogenation methods as otherwise described herein, the method is carried out at a temperature within the range of about 400° C. to about 700° C., or about 400° C. to about 650° C., or about 400° C. to about 600° C., or about 400° C. to about 550° C., or about 450° C. to about 750° C., or about 500° C. to about 750° C., or about 550° C. to about 750° C., or about 600° C. to about 750° C., or about 450° C. to about 700° C., or about 500° C. to about 650° C.

In certain embodiments of the dehydrogenation methods as otherwise described herein, the method is carried out at a pressure within the range of about 0.1 bar to about 1 bar. For example, in certain embodiments of the dehydrogenation methods as otherwise described herein, the methods is carried out at a pressure within the range of about 0.1 bar to about 0.9 bar, or about 0.1 bar to about 0.8 bar, or about 0.1 bar to about 0.7 bar, or about 0.1 bar to about 0.6 bar, or about 0.1 bar to about 0.5 bar, or about 0.2 bar to about 1 bar, or about 0.3 bar to about 1 bar, or about 0.4 bar to about 1 bar, or about 0.5 bar to about 1 bar, or about 0.2 bar to about 0.9 bar, or about 0.3 bar to about 0.8 bar, or about 0.4 bar to about 0.7 bar.

EXAMPLES

The Examples that follow are illustrative of specific embodiments of the invention, and various uses thereof. They are set forth for explanatory purposes only, and are not to be taken as limiting the invention.

Example 1. Ga Catalyst Preparation

Catalyst A1 was made by impregnation of a La—Zr mixed oxide support (NorPro, SZ61156) with an aqueous solution containing 14.77 g Ga(NO$_3$)$_3$, 0.08 g Pt(NH$_3$)$_4$(NO$_3$)$_2$, 0.23 g KNO$_3$, and 7.3 g DI-water by incipient wetness. The catalyst was dried in air at 120° C. for 5 hours and calcined at 550° C. in air for 4 hours.

Catalyst A2 was made by impregnation of a Si—Zr mixed oxide support (NorPro, SZ61152) with an aqueous solution containing 14.77 g Ga(NO$_3$)$_3$, 0.07 g Pt(NH$_3$)$_4$(NO$_3$)$_2$, 0.23 g KNO$_3$, and 8.9 g DI-water by incipient wetness. The catalyst was dried in air at 120° C. for 5 hours and calcined at 550° C. in air for 4 hours.

Catalyst A3 was made by impregnation of a Si—Zr mixed oxide support (NorPro, SZ61152) with an aqueous solution containing 10.71 g Ga(NO$_3$)$_3$, 0.06 g Pt(NH$_3$)$_4$(NO$_3$)$_2$, 0.21 g KNO$_3$, and 8.86 g DI-water by incipient wetness. The catalyst was dried in air at 120° C. for 5 hours and calcined at 550° C. in air for 4 hours.

Catalyst A4 was made by impregnation of a Ti—Zr mixed oxide support (NorPro, SZ311140) with an aqueous solution containing 10.70 g Ga(NO$_3$)$_3$, 0.22 g KNO$_3$, 0.060 g Pt(NH$_3$)$_4$(NO$_3$)$_2$, and 12.93 g DI-water by incipient wetness. The catalyst was dried in air at 120° C. for 2 hours and calcined at 550° C. in air for 4 hours.

Catalyst A5 was made by impregnation of a Ce—Zr mixed oxide support (MelChemical, XZO 1289/01) with an aqueous solution containing 2.33 g Ga(NO$_3$)$_3$, 0.16 g KNO$_3$, 0.050 g Pt(NH$_3$)$_4$(NO$_3$)$_2$, and 7.36 g DI-water by incipient wetness. The catalyst was dried in air at 120° C. for 16 hours and calcined at 550° C. in air for 4 hours.

Catalyst A6 was made by impregnation of a La—Zr mixed oxide support (NorPro, SZ61156) with an aqueous solution containing 14.71 g Ga(NO$_3$)$_3$, 0.22 g KNO$_3$, 0.0654 g Pt(NH$_3$)$_4$(NO$_3$)$_2$, 3.95 g Mg(NO$_3$)$_2$, and 7.35 g DI-water by incipient wetness. The catalyst was dried in air at 120° C. for 16 hours and calcined at 600° C. in air for 4 hours.

Catalyst A7 was made by impregnation of a Si—Zr mixed oxide support (NorPro, SZ61152) with an aqueous solution containing 3.34 g Ga(NO$_3$)$_3$, 0.21 g KNO$_3$, 0.06 g Pt(NH$_3$)$_4$(NO$_3$)$_2$, and 8.85 g DI-water by incipient wetness. The catalyst was died in air at 120° C. for 16 hours and calcined at 550° C. in air for 4 hours.

A comparative, alumina-supported gallium Catalyst C1 was prepared according to conventional methods.

TABLE 1

Ga Catalyst Compositions

| | Mixed Oxide Support | | | | Impregnated Materials | | | |
| --- | --- | --- | --- | --- | --- | --- | --- | --- |
| | | | | | Ga | Pt | K | Mg |
| Cat. | Oxide | wt. % | Oxide | wt. % | (wt. %) | (wt. %) | (wt. %) | (wt. %) |
| A1 | La$_2$O$_3$ | 10 | ZrO$_2$ | 90 | 12 | 0.1 | 0.25 | — |
| A2 | SiO$_2$ | 3.3 | ZrO$_2$ | 96.7 | 12 | 0.1 | 0.25 | — |
| A3 | SiO$_2$ | 3.3 | ZrO$_2$ | 96.7 | 9 | 0.1 | 0.25 | — |
| A4 | TiO$_2$ | 40 | ZrO$_2$ | 60 | 9 | 0.1 | 0.25 | — |
| A5 | CeO$_2$ | 16.5 | ZrO$_2$ | 83.5 | 3 | 0.1 | 0.25 | — |
| A6 | La$_2$O$_3$ | 10 | ZrO$_2$ | 90 | 12 | 0.1 | 0.25 | 1 |
| A7 | SiO$_2$ | 3.3 | ZrO$_2$ | 96.7 | 3 | 0.1 | 0.25 | — |
| C1 | Al$_2$O$_3$ | 100 | — | — | 3 | — | 0.1 | — |

Example 2. Ce-Comprising Ga Catalyst Preparation

Catalyst B1 was made by impregnation of a Si—Zr mixed oxide support (NorPro, SZ61152) with an aqueous solution containing 5.18 g Ga(NO$_3$)$_3$, 0.12 g Pt(NH$_3$)$_4$(NO$_3$)$_2$, 0.95 g Ce(NO$_3$)$_3$·6H$_2$O, 0.22 g KNO$_3$, and 3.74 g Mg(NO$_3$)$_2$, and 9.0 g DI-water by incipient wetness. The catalyst was dried at 120° C. for 16 hours and calcined at 600° C. in air for 4 hours.

TABLE 2

Ce-Comprising Ga Catalyst Compositions

| | Mixed Oxide Support | | | | Impregnated Materials | | | | |
| --- | --- | --- | --- | --- | --- | --- | --- | --- | --- |
| | | | | | Ga | Pt | Ce | K | Mg |
| Cat. | Oxide | wt. % | Oxide | wt. % | (wt. %) | (wt. %) | (wt. %) | (wt. %) | (wt. %) |
| B1 | La$_2$O$_3$ | 10 | ZrO$_2$ | 90 | 4.5 | 0.1 | 1 | 0.25 | 1 |

Example 3. Comparative Catalyst Preparation

Catalyst C2 was made by impregnation of a La—Zr mixed oxide support (NorPro, SZ61156) with an aqueous solution containing 0.070 g RuCl$_3$, and 7.32 g DI-water by incipient wetness. The catalyst was dried at 120° C. for 16 hours and calcined at 550° C. in air for 4 hours.

Catalyst C3 was made by impregnation of a Si—Zr mixed oxide support (NorPro, SZ61152) with an aqueous solution containing 0.080 g RuCl$_3$, and 8.84 g DI-water by incipient wetness. The catalyst was dried at 120° C. for 16 hours and calcined at 550° C. in air for 4 hours.

Catalyst C4 was made by impregnation of a Ti—Zr mixed oxide support (Norpro, SZ311140) with an aqueous solution containing 0.080 g $RuCl_3$, and 12.97 g DI-water by incipient wetness. The catalyst was dried at 120° C. for 2 hours and calcined at 550° C. in air for 4 hours.

C5 was made by impregnation of a La—Zr mixed oxide support (NorPro, SZ61156) with an aqueous solution containing 0.16 g $RuCl_3$, and 7.35 g DI-water by incipient wetness. The catalyst was dried at 120° C. for 16 hours and calcined at 550° C. in air for 4 hours.

TABLE 3

Comparative Catalyst Compositions

| | Mixed Oxide Support | | | | Impregnated Materials Ru |
|---|---|---|---|---|---|
| Cat. | Oxide | wt. % | Oxide | wt. % | (wt. %) |
| C2 | $La_2O_3$ | 10 | $ZrO_2$ | 90 | 0.1 |
| C3 | $SiO_2$ | 3.3 | $ZrO_2$ | 96.7 | 0.1 |
| C4 | $TiO_2$ | 40 | $ZrO_2$ | 60 | 0.1 |
| C5 | $La_2O_3$ | 10 | $ZrO_2$ | 90 | 0.2 |

Example 4. Isobutane Dehydrogenation

Catalyst compositions prepared according to Examples 1-3 were tested as prepared in a fixed-bed reactor. A feed containing 100 mol. % isobutane was passed over a 15 mL catalyst bed at a total pressure of 0.5 bar, at 2.1 $h^{-1}$ Liquid Hourly Space Velocity (LHSV) at a temperature within the range of 540-600° C. The product effluent concentration at the reactor outlet was monitored with an in-line gas chromatograph (GC). Results are provided in Table 4, below.

TABLE 4

Isobutane Dehydrogenation

| T (° C.) | Isobutane Conversion (wt. %) | Isobutylene Selectivity (wt. %) |
|---|---|---|
| C1 | 540 | 17.2 | 84.7 |
| A1 | 540 | 47.2 | 80.7 |
| A2 | 540 | 46.4 | 66.6 |
| A3 | 540 | 48.5 | 66.6 |
| A4 | 540 | 35.7 | 72.6 |
| A5 | 540 | 25.6 | 83.9 |
| A6 | 540 | 43.5 | 85.7 |
| B1 | 540 | 35.7 | 84.8 |
| C1 | 540 | 33.1 | 78.6 |
| C2 | 540 | 11.1 | 74.8 |
| C3 | 540 | 16.3 | 71.9 |
| C4 | 540 | 28.2 | 71.2 |

The results, shown in Table 4, demonstrate that the Ga-containing catalysts provide hydrocarbon dehydrogenation efficiency comparable to or better than conventional alumina-supported catalysts, and zirconium-support catalysts lacking gallium.

Example 5. Propane Dehydrogenation

Catalyst compositions prepared according to Examples 1-3 were tested as prepared in a fixed-bed reactor. A feed containing 100 mol. % propane was passed over a 15 ml catalyst bed at a total pressure of 0.5 bar, at 2.1 $h^{-1}$ Liquid Hourly Space Velocity (LHSV), at a temperature within the range of 540-600° C. The product effluent concentration at the reactor outlet was monitored with an on-line gas chromatograph (GC). Results are provided in Table 5, below.

TABLE 5

Propane Dehydrogenation

| | T (° C.) | Propane Conversion (wt. %) | Propylene Selectivity (wt. %) |
|---|---|---|---|
| C1 | 540 | 11.0 | 87.8 |
| A3 | 540 | 24.9 | 78.6 |
| A4 | 540 | 30.0 | 67.9 |
| A5 | 540 | 15.4 | 74.6 |
| B1 | 540 | 18.6 | 78.1 |
| C2 | 540 | 17.2 | 57.1 |
| C3 | 540 | 9.9 | 55.4 |
| C4 | 540 | 16.5 | 72.8 |

The results, shown in Table 5, show that the catalysts provide hydrocarbon dehydrogenation efficiency comparable to or better than conventional alumina-supported catalysts, and zirconium-support catalysts lacking gallium.

Example 6. Propane Dehydrogenation

Catalyst compositions C2-C5, a copper-comprising catalyst lacking gallium prepared in a manner similar to that of Example 3 (C6, shown in Table 6, below), a support lacking any impregnated material (C7, shown in Table 6, below) and a commercially available alumina-supported chromium catalyst were tested in a fixed-bed reactor in a manner similar to that of Example 4, at a temperature of 538° C. Activity and selectivity results are provided in FIGS. 1-2.

TABLE 6

Comparative Catalyst Compositions

| | Mixed Oxide Support | | | | Impregnated Materials Cu |
|---|---|---|---|---|---|
| Cat. | Oxide | wt. % | Oxide | wt. % | (wt. %) |
| C6 | $La_2O_3$ | 10 | $ZrO_2$ | 90 | 0.1 |
| C7 | $La_2O_3$ | 10 | $ZrO_2$ | 90 | |

Figure 2:
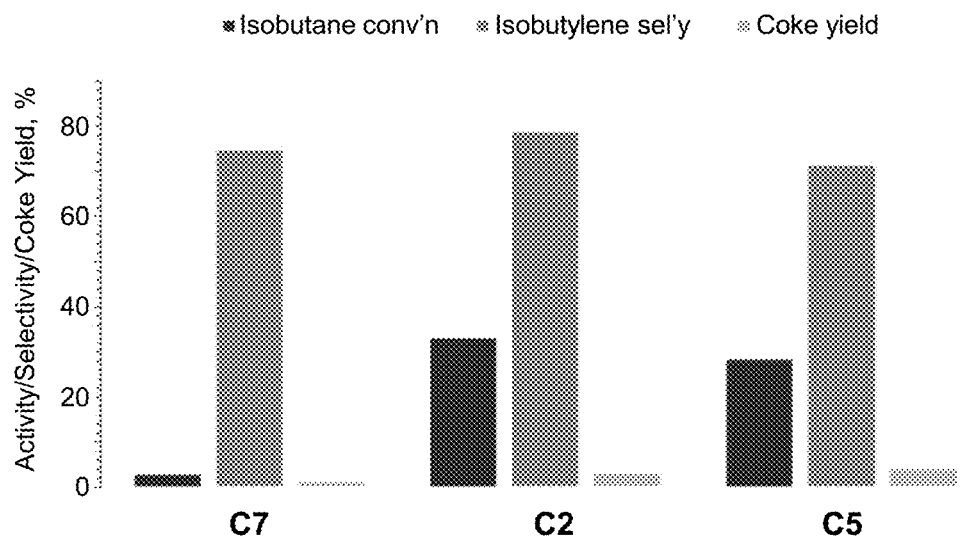
FIG. 2 is a bar graph showing (left-to-right in each set of bars) isobutane dehydrogenation conversion, isobutylene selectivity, and coke yield data for a variety of catalysts described herein.

Of the chromium-free catalyst compositions tested, catalyst C2 showed the best isobutane conversion, 33%, but still showed an activity 20% lower than that of the commercial alumina-supported chromium-catalysts (see FIG. 1). A ruthenium loading of 0.1 wt. % (C2) improved isobutane conversion from 2.6% (C7) to 33%, but at 0.2 wt. % (C5), isobutane conversion decreased to 28.2% (see FIG. 2). Additionally, coke yield increased with ruthenium loading (see FIG. 2).

Example 7. Propane Dehydrogenation

Catalyst compositions A1-A2, catalysts prepared in a manner similar to that of Example 1 (A7-A9, shown in Table 6, below), and a commercially available chromium-aluminum catalyst were tested in a fixed-bed reactor in a manner similar to that of Example 4, at a temperature of 540° C. Activity and selectivity results are provided in FIG. 3.

TABLE 7

Ga Catalyst Compositions

| | Mixed Oxide Support | | Impregnated Materials | | | |
|---|---|---|---|---|---|---|
| | | | Ga | Pt | K | Mg |
| Cat. | Oxide | wt. % | Oxide | wt. % | (wt. %) | (wt. %) | (wt. %) | (wt. %) |
| A7 | La$_2$O$_3$ | 10 | ZrO$_2$ | 90 | 3 | 0.1 | 0.25 | — |
| A8 | La$_2$O$_3$ | 10 | ZrO$_2$ | 90 | 6 | 0.1 | 0.25 | — |
| A9 | La$_2$O$_3$ | 10 | ZrO$_2$ | 90 | 9 | 0.1 | 0.25 | — |

Figure 5:
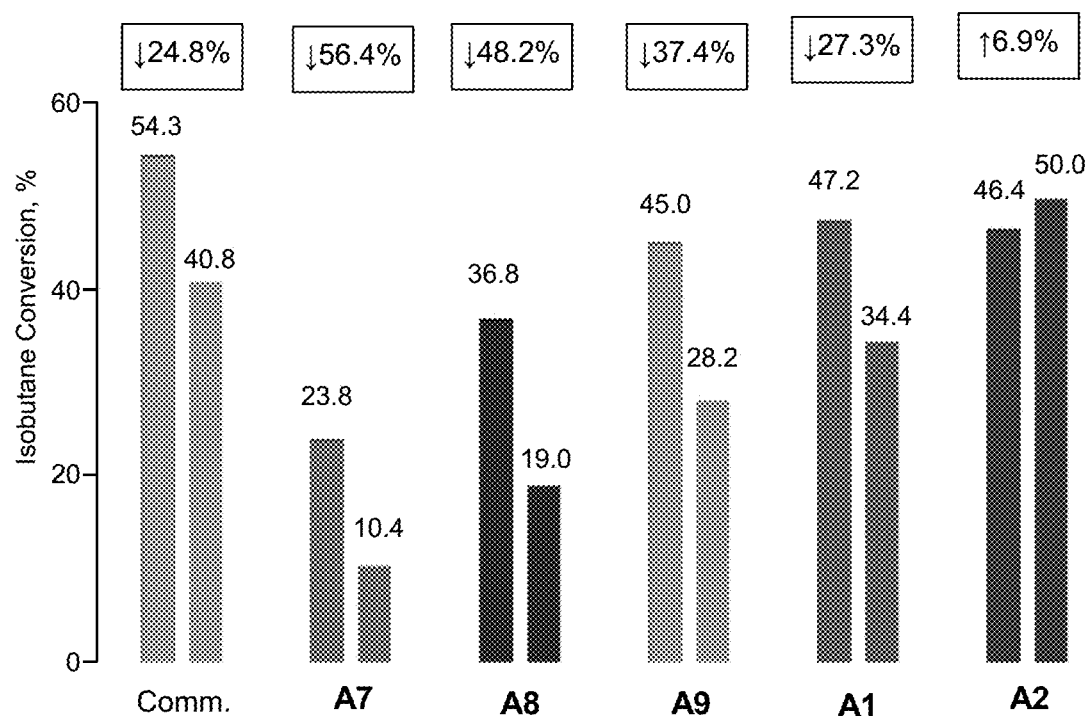
FIG. 5 is a bar graph showing (left-to-right in each set of bars) isobutane dehydrogenation conversion before and after mildly aging (650° C. for 300 cycles) for a variety of catalysts described herein.

As shown in graph of FIG. 5, as the Ga loading increased from 3 wt. % (A7) to 6 wt. % (A8), isobutane conversion increased from 23.8% to 36.8% (an increase of 54.6%). As Ga loading increased to 9 wt. % (A9), isobutane conversion increased to 45% (an increase of 22.3%). As the Ga loading increased to 12 wt. % (A1), isobutane conversion increased by only 0.5%, suggesting a plateau in catalyst activity. Isobutane selectivity decreased approximately linearly, from 85.8% to 80.7%, as Ga loading increased from 3 wt. % (A7) to to 12 wt. % (A1).

Figure 3:
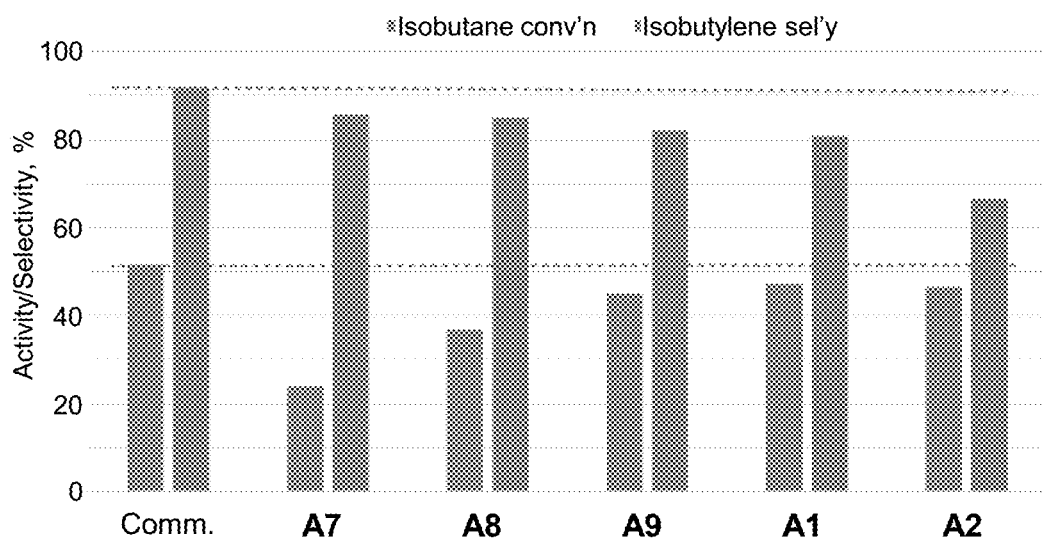
FIG. 3 is a bar graph showing (left-to-right in each set of bars) isobutane dehydrogenation conversion and isobutylene selectivity for a variety of catalysts described herein.

The activity and selectivity of A1, which showed the best performance of the chromium-free catalyst compositions of FIG. 3, was 4% and 11% lower, respectively, than that of the alumina supported chromium catalyst. Catalyst A1, supported on La—Zr, showed similar activity to, but 14.2% higher selectivity than that of A2, supported on Si—Zr.

Example 8. Propane Dehydrogenation Cycling

Figure 4:
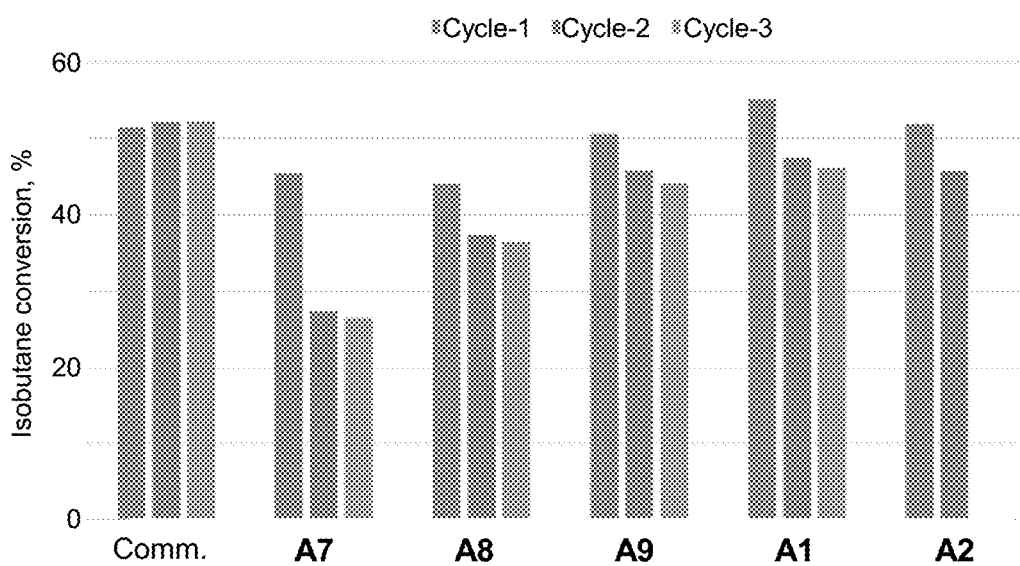
FIG. 4 is a bar graph showing isobutane conversion for (left-to-right in each set of bars) the first cycle, the second cycle, and the third cycle of isobutane dehydrogenation, for a variety of catalysts described herein.

The catalyst compositions of Example 7 were tested in a manner similar to that of Example 4, for three consecutive cycles. Activity results for each cycle are provided in FIG. 4. As shown in FIG. 4, the chromium-free catalysts showed good start-of-run (SOR) stability.

Example 9. Catalyst Aging

To evaluate the long-term stability of the catalyst compositions, catalysts A1-A2 and A7-A9 and a commercially available chromium-aluminum catalyst were subjected to mild aging at 650° C. for 300 redox cycles. The activity results before and after aging are provided in FIG. 5. Most catalysts showed varying degrees of activity loss, though isobutane conversion of catalyst A2 increased by ~4%. Notably, the absolute change in isobutane conversion after aging was similar among the La—Zr-supported catalysts (A7-A9, A1); accordingly, the catalyst compositions with high Ga loadings showed relatively lower deactivation. The absolute and relative decreases in isobutylene yield for the La—Zr-supported catalysts was similar to (A7, A8) or better than (A9, A1) those of the comparative chromium-aluminum catalyst. The isobutylene yield of catalyst A2 before aging was ~20% lower than the chromium-aluminum catalyst, due to its relatively lower selectivity. After aging, however, the isobutylene yield of catalyst A2 increased, while that of the alumina supported chromium catalyst decreased.

Additional aspects of the disclosure are provided in the following numbered embodiments, which can be combined in any logically- and technically-consistent manner.

Embodiment 1. A calcined dehydrogenation catalyst composition comprising a mixed oxide support comprising at least about 50 wt. % of zirconium oxide, the mixed oxide support being present in the composition in an amount within the range of about 40 wt. % to about 99.9 wt. %; and disposed on the support, gallium, present in the composition in an amount within the range of about 0.1 wt. % to about 30 wt % (e.g., in the form of gallium oxide of any crystalline/amorphous phase), calculated as Ga$_2$O$_3$ on a calcined basis.

Embodiment 2. The catalyst composition of embodiment 1, wherein gallium is present in an amount within the range of about 1 wt. % to about 20 wt. %, calculated as Ga$_2$O$_3$ on a calcined basis.

Embodiment 3. The catalyst composition of embodiment 1, wherein gallium is present in an amount within the range of about 3 wt. % to about 15 wt. %, calculated as Ga$_2$O$_3$ on a calcined basis.

Embodiment 4. The catalyst composition of embodiment 1, further comprising, disposed on the support, one or more primary promoters selected from platinum, iridium, lanthanum, zinc, iron, rhodium, palladium, and ruthenium, present in the composition in an amount within the range of about 0.01 wt. % to about 5 wt. %, calculated as oxide on a calcined basis.

Embodiment 5. The catalyst composition of any of embodiments 1-4, wherein a platinum promoter is disposed on the support in an amount within the range of about 0.05 wt. % to about 0.5 wt. %, calculated as PtO$_2$ on a calcined basis.

Embodiment 6. The catalyst composition of any of embodiments 1-5, wherein a platinum promoter is disposed on the support in an amount within the range of about 0.01 wt. % to about 1 wt. %, calculated as PtO$_2$ on a calcined basis.

Embodiment 7. The catalyst composition of any of embodiments 1-6, further comprising, disposed on the support, one or more secondary promoters selected from potassium, sodium, cesium, lithium, calcium, magnesium, strontium, and barium, present in the composition in an amount within the range of about 0.01 wt. % to about 15 wt. %, for example, about 0.1 wt. % to about 10 wt. %, or about 0.01 wt. % to about 5 wt. %, calculated as oxide on a calcined basis.

Embodiment 8. The catalyst composition of any of embodiments 1-7, wherein potassium is disposed on the support in an amount within the range of about 0.01 wt. % to about 2 wt. %, calculated as K$_2$O on a calcined basis.

Embodiment 9. The catalyst composition of any of embodiments 1-8, wherein magnesium is disposed on the support in an amount within the range of about 0.01 wt. % to about 2 wt. %, calculated as MgO on a calcined basis.

Embodiment 10. The catalyst composition of any of embodiments 1-9, wherein cerium is disposed on the support in an amount within the range of about 0.5 wt. % to about 15 wt. %, for example, about 0.5 wt. % to about 10 wt. %, or about 0.5 wt. % to about 5 wt. %, calculated as CeO$_2$ on a calcined basis.

Embodiment 11. The catalyst composition of any of embodiments 1-10, wherein the mixed oxide support is present in the overall catalyst composition in an amount within the range of about 70 wt. % to about 97 wt. %.

Embodiment 12. The catalyst composition of any of embodiments 1-11, wherein the mixed oxide support comprises at least about 80 wt. %, at least about 90 wt. %, or at least about 95 wt. % of zirconium oxide.

Embodiment 13. The catalyst composition of any of embodiments 1-12, wherein the mixed oxide support comprises an oxide of one or more of lanthanum, cerium, silicon, titanium, tungsten, and yttrium.

Embodiment 14. The catalyst composition of claim 13, wherein the total amount of oxides of zirconium, lanthanum, cerium, silicon, titanium, tungsten, and yttrium in the mixed oxide support is at least 95 wt. %, for example, at least 98 wt. %.

Embodiment 15. The catalyst composition of any of embodiments 1-12, wherein the mixed oxide support comprises an oxide of one or more of lanthanum, cerium, titanium, tungsten, and yttrium.

Embodiment 16. The catalyst composition of embodiment 15, wherein the total amount of oxides of zirconium, lanthanum, cerium, titanium, tungsten, and yttrium in the mixed oxide support is at least 95 wt. %, for example, at least 98 wt. %.

Embodiment 17. The catalyst composition of any of embodiments 1-16, wherein the mixed oxide support comprises about 80 wt. % to about 99 wt. % of zirconium oxide; and about 1 wt. % to about 20 wt. % of an oxide of one or more of lanthanum, silicon, and cerium.

Embodiment 18. The catalyst composition of any of embodiments 1-16, wherein the mixed oxide support comprises about 50 wt. % to about 75 wt. % of zirconium oxide; and about 25 wt. % to about 50 wt. % of titanium oxide.

Embodiment 19. The catalyst composition of any of embodiments 1-18, wherein the mixed oxide support comprises less than about 2 wt. %, for example, less than about 1 wt. %, or less than about 0.1 wt. %, of silica.

Embodiment 20. The catalyst composition of any of embodiments 1-19, wherein the mixed oxide support comprises less than about 2 wt. %, for example, less than about 1 wt. %, or less than about 0.1 wt. %, of alumina.

Embodiment 21. The catalyst composition of any of embodiments 1-20, wherein the composition comprises the mixed oxide support, present in the composition in an amount within the range of about 75 wt. % to about 99 wt. %, or about 83.5 wt. % to about 98.85 wt. %; gallium, present in the composition in an amount within the range of about 1 wt. % to about 20 wt. %, or about 1 wt. % to about 15 wt. %, calculated as $Ga_2O_3$ on a calcined basis; and a platinum primary promoter, present in the composition in an amount within the range of about 0.05 wt. % to about 1 wt. %, or about 0.05 wt. % to about 0.5 wt. %, calculated as $PtO_2$ on a calcined basis.

Embodiment 22. The catalyst composition of embodiment 21, wherein the composition further comprises a potassium secondary promoter, present in the composition in an amount within the range of about 0.1 wt. % to about 2 wt. %, or about 0.1 wt. % to about 1 wt. %, calculated as $K_2O$ on a calcined basis.

Embodiment 23. The catalyst composition of any of embodiments 1-22, wherein the composition comprises less than 0.2 wt. % of chromium.

Embodiment 24. The catalyst composition of any of embodiments 1-23, wherein the composition comprises less than 0.2 wt. % of iron.

Embodiment 25. The catalyst composition of any of embodiments 1-24, wherein the composition comprises less than 1 wt. % of the lanthanides other than lanthanum and cerium.

Embodiment 26. The catalyst composition of any of embodiments 1-25, wherein the total amount of the mixed oxide support, gallium oxide, the one or more primary promoters, the one or more secondary promoters, and cerium oxide is at least about 80 wt. %, at least about 85 wt. %, at least about 90 wt. %, at least about 95 wt. %, at least about 97.5 wt. %, or at least about 99 wt. % of the catalyst composition.

Embodiment 27. A method for preparing a dehydrogenation catalyst composition according to any of embodiments 1-26, the method comprising providing a mixed oxide support comprising at least about 50 wt. % of zirconium oxide; disposing on the mixed oxide support one or more sources of gallium and of any primary or secondary promoters and cerium to be present in the catalyst composition; and calcining the supported composition so formed.

Embodiment 28. A method according to embodiment 27, wherein the calcination temperature is within the range of about 250° C. to about 850° C.

Embodiment 29. A method according to embodiment 27, wherein the calcination temperature is within the range of about 400° C. to about 700° C.

Embodiment 30. A method according to any of embodiments 27-29, wherein the one or more sources of gallium and of any primary or secondary promoters and cerium to be present in the catalyst composition are disposed on the mixed oxide support using impregnation.

Embodiment 31. A catalyst composition according to any of embodiments 1-26 made by a method of any of claims 26-29.

Embodiment 32. A method for dehydrogenating hydrocarbons, the method comprising contacting a hydrocarbon feed with the catalyst composition of any of embodiments 1-26 or 31.

Embodiment 33. A method according to embodiment 32, wherein the hydrocarbon feed comprises one or more $C_3$-$C_5$ alkanes.

Embodiment 34. A method according to embodiment 33, wherein the hydrocarbon feed comprises isobutane.

Embodiment 35. A method according to embodiment 33, wherein the hydrocarbon feed comprises propane.

Embodiment 36. A method according to any of embodiments 32-35, wherein the hydrocarbon feed is contacted with the catalyst at a space velocity within the range of about 0.1 $h^{-1}$ to about 2 $h^{-1}$ LHSV.

Embodiment 37. A method according to any of embodiments 32-36, wherein the dehydrogenation is conducted at a temperature within the range of about 400° C. to about 750° C.

Embodiment 38. A method according to any of embodiments 32-37, wherein the dehydrogenation is conducted at a pressure within the range of about 0.1 bar to about 1 bar.

We claim:

1. A calcined dehydrogenation catalyst comprising a mixed oxide support comprising at least 80 wt. % to 99 wt. % of zirconium oxide and 1 wt. % to 20 wt. % of one or more of lanthanum oxide, silicon oxide and cerium oxide, the mixed oxide support being present in the composition in an amount within the range of 70 wt. % to 95 wt. %; and disposed on the support, gallium, present in the composition in an amount within the range of 7.5 wt. % to 30 wt. %, calculated as $Ga_2O_3$ on a calcined basis; and one or more primary promoters selected from platinum, rhodium, palladium, and ruthenium, present in the composition in an amount within the range of 0.01 wt. % to 0.5 wt. %, calculated as oxide on a calcined basis.

2. The catalyst composition of claim 1, wherein a platinum primary promoter is disposed on the support in an amount within the range of 0.01 wt. % to % 0.5 wt. %, calculated as $PtO_2$ on a calcined basis.

3. The catalyst composition of claim 1, further comprising, disposed on the support, one or more secondary promoters selected from potassium, sodium, cesium, lithium, calcium, magnesium, strontium, and barium, present in the composition in an amount within the range of 0.01 wt. % to 2 wt. %, calculated as oxide on a calcined basis.

4. The catalyst composition of claim 1, wherein potassium is disposed on the support in an amount within the range of 0.01 wt. % to 2 wt. %, calculated as $K_2O$ on a calcined basis and/or magnesium is disposed on the support in an amount within the range of 0.01 wt. % to 2 wt. %, calculated as MgO on a calcined basis.

5. The catalyst composition of claim 1, wherein cerium is disposed on the support in an amount within the range of 0.5 wt. % to 15 wt. %, calculated as $CeO_2$ on a calcined basis.

6. The catalyst composition of claim 1, wherein a total amount of oxides of zirconium, lanthanum, cerium, silicon, titanium, tungsten, and yttrium in the mixed oxide support is at least 95 wt. %.

7. The catalyst composition of claim 1, wherein the mixed oxide support comprises less than 2 wt. % of silica.

8. The catalyst composition of claim 1, wherein the mixed oxide support comprises less wt. % of alumina.

9. The catalyst composition of claim 1, wherein the composition comprises the mixed oxide support, present in the composition in an amount within the range of 83.5 wt. % to 98.85 wt. %; and the primary promoter is platinum, present in the composition in an amount within the range of 0.05 wt. % to 0.5 wt. %, calculated as $PtO_2$ on a calcined basis.

10. The catalyst composition of claim 9, wherein the composition further comprises a potassium secondary promoter, present in the composition in an amount within the range of 0.1 wt. % to 2 wt. % calculated as $K_2O$ on a calcined basis.

11. The catalyst composition of claim 1, wherein the composition comprises less than 0.2 wt. % of chromium and less than 0.2 wt. % of iron.

12. The catalyst composition of claim 1, wherein a total amount of the mixed oxide support, gallium oxide, the one or more primary promoters, and the one or more secondary promoters is at least 95 wt. % of the catalyst composition.

13. A method for preparing the dehydrogenation catalyst composition according to claim 1, the method comprising providing a mixed oxide support comprising at least 50 wt. % of zirconium oxide; disposing on the mixed oxide support one or more sources of gallium and of any primary or secondary promoters and cerium to be present in the catalyst composition; and calcining the supported composition to form the dehydrogenation catalyst composition.

14. A method of dehydrogenating hydrocarbons comprising contacting a hydrocarbon feed with the dehydrogenation catalyst composition of claim 1, wherein the hydrocarbon feed comprises one or more $C_3$-$C_5$ alkanes, the hydrocarbon feed is contacted with the catalyst at a space velocity within the range of 0.1 $h^{-1}$ to 2 $h^{-1}$-LHSV, the dehydrogenation is conducted at a temperature within the range of 400° C. to 750° C. and the dehydrogenation is conducted at a pressure within the range of 0.1 bar to 1 bar.

* * * * *